(12) United States Patent
Sayama et al.

(10) Patent No.: US 6,648,868 B2
(45) Date of Patent: Nov. 18, 2003

(54) DISPOSABLE DIAPER

(75) Inventors: Yasushi Sayama, Kagawa (JP);
Toshifumi Otsubo, Kagawa (JP);
Yasushi Inoue, Kagawa (JP)

(73) Assignee: Uni-Charm Corporation, Ehime-ken (JP)

( * ) Notice: Subject to any disclaimer, the term of this patent is extended or adjusted under 35 U.S.C. 154(b) by 3 days.

(21) Appl. No.: 09/131,715

(22) Filed: Aug. 10, 1998

(65) Prior Publication Data

US 2001/0016723 A1 Aug. 23, 2001

(30) Foreign Application Priority Data

Sep. 29, 1997 (JP) ................................ 9-264163

(51) Int. Cl.[7] .......................... A61F 13/15; A61F 13/20
(52) U.S. Cl. .............................. 604/385.22; 604/385.3; 604/392; 604/394; 604/396
(58) Field of Search .................... 604/385.1, 385.2, 604/386, 393–399, 402, 385.01, 385.11, 385.21, 385.22, 385.24–385.3

(56) References Cited

U.S. PATENT DOCUMENTS

| | | | | |
|---|---|---|---|---|
| 2,584,898 A | * | 2/1952 | McConnell | 604/398 |
| 3,077,193 A | * | 2/1963 | Mann | 604/398 |
| 3,704,710 A | * | 12/1972 | Fifer | 604/398 |
| 3,756,878 A | * | 9/1973 | Willot | 604/398 |
| 4,205,679 A | * | 6/1980 | Repke et al. | 604/394 |
| 4,747,846 A | * | 5/1988 | Boland et al. | 604/385.2 |
| 4,892,598 A | * | 1/1990 | Stevens et al. | 604/385.2 |
| 4,936,840 A | | 6/1990 | Proxmire | |
| 2002/0143313 A1 | * | 10/2002 | Tsuji et al. | 604/385.03 |
| 2002/0147438 A1 | * | 10/2002 | Tanaka et al. | 604/392 |
| 2002/0147439 A1 | * | 10/2002 | Tanaka et al. | 604/398 |

FOREIGN PATENT DOCUMENTS

| | | | | |
|---|---|---|---|---|
| GB | 2253131 | * | 9/1992 | 604/385.2 |
| GB | 2 284 741 | | 6/1995 | |
| WO | 95/06451 | * | 3/1995 | |

OTHER PUBLICATIONS

Copy of European Search Report dated Jun. 19, 2000.

* cited by examiner

*Primary Examiner*—Karin Reichle
(74) *Attorney, Agent, or Firm*—Butzel Long

(57) ABSTRACT

A disposable diaper includes a cover member having an hourglass-shape and a-separate liquid-absorbent member composed of a liquid-permeable topsheet, a liquid-impermeable backsheet and a liquid-absorbent core. The cover member has an elastic stretchability along the upper ends of front and waist regions, and these front and rear waist regions are connected or connectable along transversely opposite side edges thereof. The liquid-absorbent member includes first and second elastically stretchable members that extend circumferentially across portions of the front and rear waist regions lying immediately above the crotch region. Longitudinally opposite ends of these elastically stretchable members are bonded to the transversely opposite side edges of the cover member.

10 Claims, 3 Drawing Sheets

DISPOSABLE DIAPER

BACKGROUND OF THE INVENTION

This invention relates to disposable diapers for absorbing and containing urine and other body exudates and, more particularly, to such disposable diapers of the so-called open type or so-called pull-on type.

Disposable diapers generally comprising a liquid-permeable topsheet, a liquid-impermeable backsheet and a liquid-absorbent member disposed between these two sheets, of the so-called open type and of the so-called pull-on type are well known in the art. The former has an hourglass-shape as viewed in its plan view and has front and rear waist regions that are adapted to be separably connected together along their transversely opposite side edges. The latter, on the other hand, has front and rear waist regions that are adapted to be separably or inseparably connected together along their transversely opposite side edges. In these known diapers, at least one of the front and rear waist regions is provided along its longitudinal end with elastically stretchable members that extend circumferentially of the waist regions. The purpose of these elastic stretchable members is to prevent the diaper from slipping down during its use and to improve the fit of the absorbent member against the wearer's body. Additionally, the waist regions are provided in their vertically middle level with auxiliary elastically stretchable members that extend circumferentially and are bonded thereto under appropriate tension. The leg-openings are also provided along their peripheral edges with elastically stretchable members.

With the above known diapers which include the elastically stretchable members around their waist-openings and leg-openings as well as at the vertically middle level of their waist regions, a good fit of the diaper to the wearer's body which is effective to prevent leakage of excretion can be achieved, however, the interior of the diaper readily becomes stuffy.

SUMMARY OF THE INVENTION

In view of the problem as described above, it is an object of the invention to provide a disposable diaper which minimizes excretion leakage and prevents the interior of the diaper from becoming stuffy.

According to this and other objects, features and characteristics, the present invention provides a disposable diaper which comprises a cover member having a front waist region, a rear waist region and a crotch region extending between the front and rear waist region, transversely opposite side edges of the crotch region being curved inwardly so that the sheet-like cover member has an hourglass-shape when said front waist region, rear waist region and crotch region are in a flat state, and a liquid-absorbent member composed of a liquid-permeable topsheet, a liquid-impermeable backsheet and a liquid-absorbent core disposed therebetween, the liquid-absorbent member extending on the inner surface of the cover member from the crotch region toward the front and rear waist regions, the cover member having an elastic stretchability circumferentially of the waist regions along the longitudinal end of at least one of the front and rear waist regions, transversely opposite side edges of the front and rear waist regions being connected or connectable to each other; and the liquid-absorbent member including elastically stretchable members that extend circumferentially under appropriate tension across portions of the front and rear waist regions lying immediately above the curved crotch region and longitudinally opposite ends of the respective elastically stretchable members are bonded to transversely opposite side edges of the respective waist regions, the elastically stretchable members being substantially connected to each other so as to form a continuous loop.

Preferably, the cover member is made of a nonwoven fabric having an elastic stretchability circumferentially of the waist regions.

According to another embodiment, the cover member has the configuration of a so-called shorts type in which the respective transversely opposite side edges of the front and rear waist regions are separably or inseparably connected to each other.

According to still another embodiment, the cover member is provided at the transversely opposite side edges or at the front and rear waist regions with means adapted to be releasably fastened one to another.

DESCRIPTION OF THE PREFERRED EMBODIMENTS

Details of a disposable diaper according to the present invention will be more fully understood from the description given hereafter with reference to the accompanying drawings.

Figure 1:
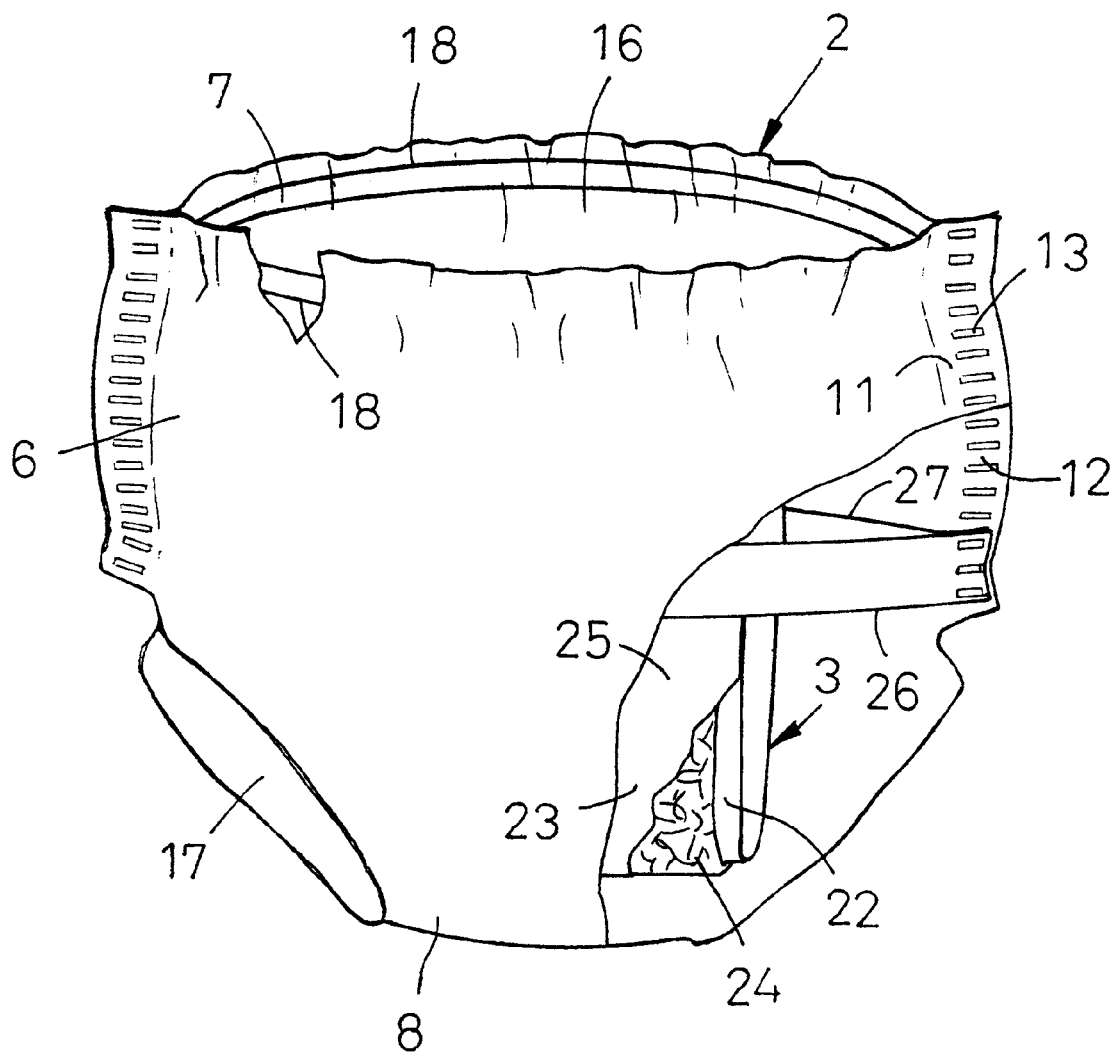
FIG. 1 is a perspective view of a partly cutaway disposable diaper according to the present invention.

A disposable diaper is shown by FIG. 1, in a perspective view as partially broken away, which comprises a cover member 2 shaped as a pair of shorts and an absorbent member 3 positioned inside the cover member 2. The cover member 2 is made of a nonwoven fabric and includes a front waist region 6, a rear waist region 7 and a crotch region 8 which extends between the front and rear waist regions 6, 7. The front and rear waist regions 6, 7 are held flat together along their transversely opposite side edges 11, 12 where they are bonded together by bonded spots 13 that are intermittently arranged in the vertical direction of each side edge 11, 12. The cover member 2 has a waist-opening 16 and a pair of leg-openings 17. An elastically stretchable member 18 is bonded under appropriate tension around the waist-opening 16 adjacent a peripheral edge of the waist-opening 16.

The liquid-absorbent member 3 has a laminate panel 25 which comprises a liquid-permeable topsheet 22, a liquid-impermeable backsheet 23 and a liquid-absorbent core 24 disposed between these two sheets 22, 23. The laminate panel 25 extends from the crotch region 8 of the cover member 2 toward the front and rear waist regions 6, 7, respectively. In the zones of the front and rear waist regions which lie immediately above the leg-openings 17 and define a part of the crotch region 8, the liquid-absorbent member 3 includes first and second belt-like elastically stretchable members 26, 27 that extend circumferentially of the waist regions from transversely opposite side edges of the laminate panel 25.

Figure 2:
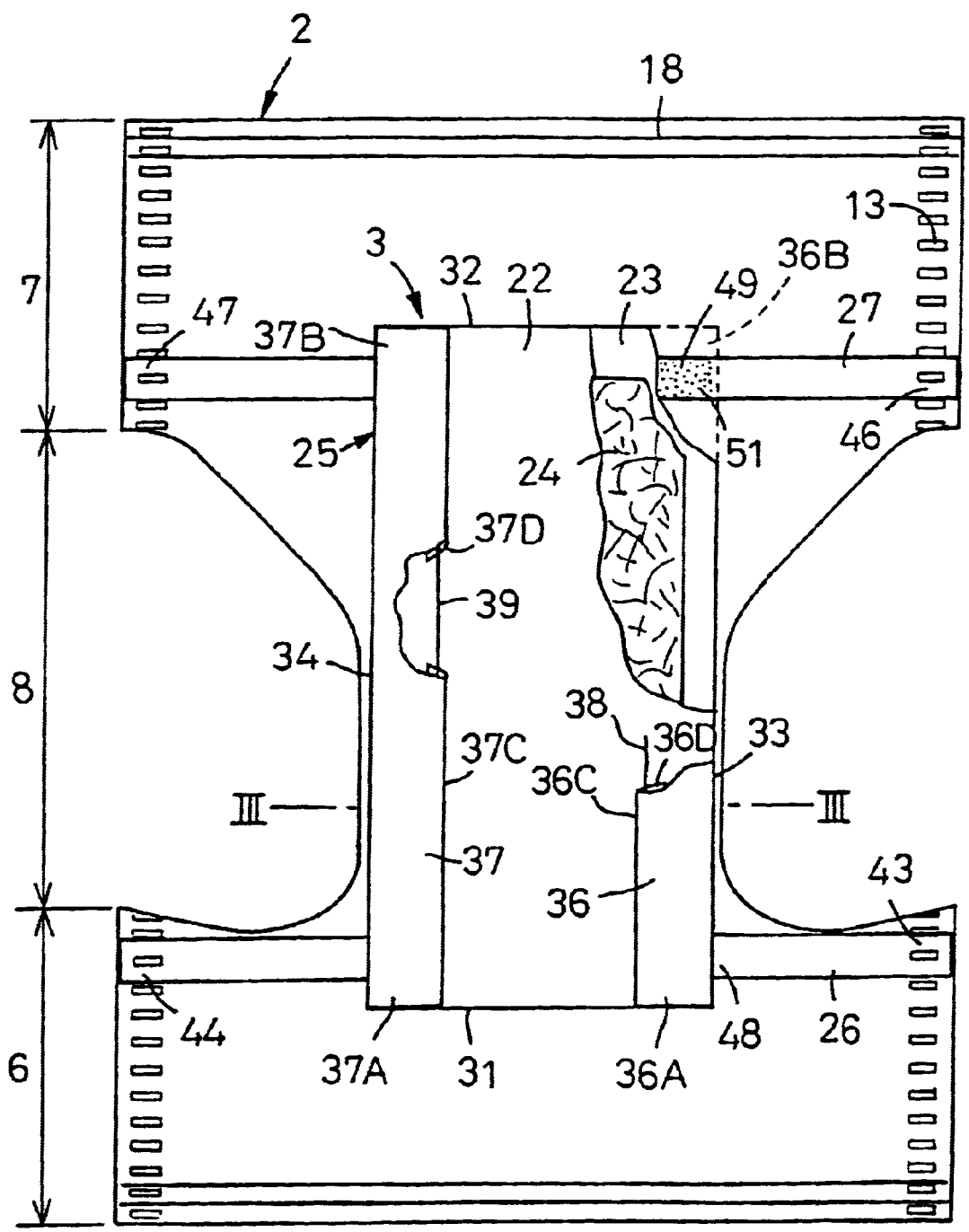
FIG. 2 is a plan view of the partly cutaway disposable diaper in its unfolded state.
Figure 3:
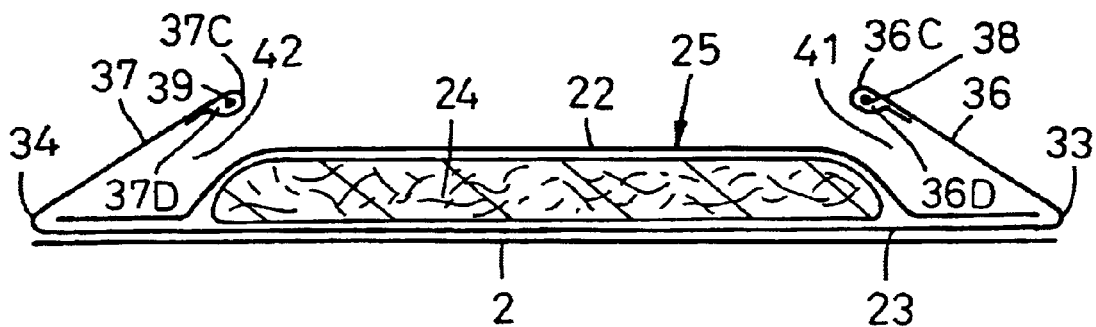
FIG. 3 is a sectional view taken along a line III—III in FIG. 2.

FIG. 2 is a partially broken away plan view showing the diaper longitudinally in an unfolded state, achieved by separating the front and rear waist region s 6, 7 of the cover member 2 illustrated in FIG. 1 along the bonded spots 13. FIG. 3 is a sectional view of the diaper taken along a line III—III in FIG. 2. The laminate panel 25 of the liquid-absorbent member 3 has the shape of a longitudinally enlarged rectangle defined by longitudinally opposite ends 31, 32 and transversely opposite side edges 33, 34. The topsheet 22 and the backsheet 23 of the laminate panel 25 are placed one upon another and bonded together by means of hot melt adhesive (not shown) along portions thereof which extend outward beyond the peripheral edges of the rectangular liquid-absorbent core 24. The backsheet 23 extends laterally beyond the side edges of the topsheet 22 and includes extensions that are folded transversely along opposite side edges 33, 34 of the laminate pad 25 and inwardly of the laminate panel 25 so as to form barrier flaps 36, 37. Longitudinally opposite ends 36A, 36B; 37A, 37B of the respective flaps 36, 37 are bonded to the topsheet 22 by means of hot melt adhesive (not shown). Elastically stretchable members 38, 39 are inserted under appropriate tension into sleeve-like portions 36D, 37D formed by respective inner side edges 36C, 37C of the barrier flaps 36, 37 and extend longitudinally of the barrier flaps 36, 37. These elastically stretchable members 38, 39 have opposite ends (not shown) which are bonded to the longitudinally opposite ends 36A, 36B; 37A, 37B of the respective barrier flaps 36, 37. In the state of the diaper as shown by FIG. 1, the elastically stretchable members 38, 39 contract and consequently pockets 41, 42 formed between the respective flaps 36, 37 and the topsheet 22 are forced to open inwardly of the laminate panel 25.

The first and second elastically stretchable members 26, 27 of the liquid-absorbent member 3 are normally under tension circumferentially of the waist regions and have opposite ends 43, 44, 46, 47 which are bonded by means of hot melt adhesive (not shown) to the inner surface of the cover member 2 at transversely opposite side edges thereof.

Longitudinally middle portions 48, 49 of the first and second elastically stretchable members 26, 27 are bonded the outer surface of the backsheet 23 by means of hot melt adhesive 51. The first and second elastically stretchable members 26, 27 are configured so that, when the diaper is raised up as shown in FIG. 1, the respective ends 43, 46 and 44, 47 are connected together to form a substantially continuous loop.

With such diaper put on the wearer's body, the elastically stretchable member 18 associated with the waist-opening is tightly placed against the upper region of the wearer's belly while the first and second elastically stretchable members 26, 27 are tightly placed against the lower region of the wearer's belly. As a consequence, even if the elastically stretchable member 18 associated with the waist-opening slips down beyond the bulge of the wearer's belly, the first and second elastically stretchable members 26, 27 can prevent the liquid-absorbent member 3 from slipping down.

The laminate panel 25 of the liquid-absorbent member 3 may be formed as compact as possible without decreasing its body fluids absorbing capacity in order to assure that the area over which it contacts the wearer's body is sufficiently reduced so as to avoid having the wearer experience a feeling of stuffiness caused by the liquid-absorbent member. Such compact laminate panel 25 is covered with the cover member 2 which prevents the wearer's hand from contacting and moving the laminate pad 25 away from its proper placement. The cover member 2 may have a size and appearance that will provide a breathable gap between the wearer's body and the cover member 2, and create the appearance like that of the ordinary clothes. However, the cover member 2 is not limited to the embodiment as has been described and illustrated. For example, a sheet having an elasticity circumferentially of the waist regions may be employed for the cover member 2 in order to place the cover member 2 tightly against the wearer's body. It is also possible to modify the embodiment described hereinabove so that the first and second elastically stretchable members 26, 27 extend between the side edges 33, 34 of the laminate panel 25 and the respective side edges of the cover member 2. Such a modification would eliminate intermediate sections 48, 49 and allow the first and second elastically stretchable members 26, 27 to shortened. In such a modification, the first and second elastically stretchable members 26, 27 will cooperate with the laminate panel 25 to form a loop.

Figure 4:
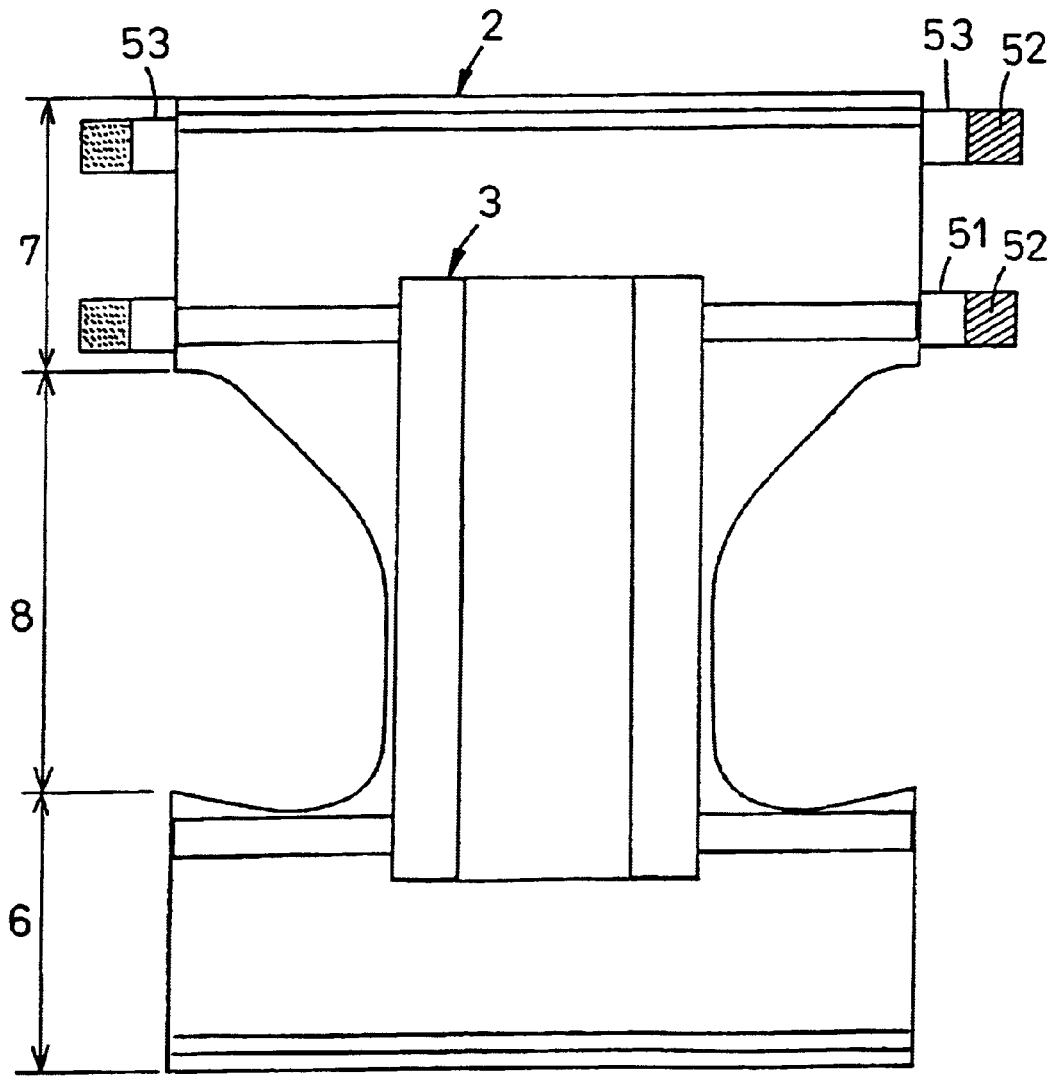
FIG. 4 is a plan view of the partly cutaway disposable diaper as a variant of the invention.

FIG. 4 is a plan view showing a variant of the disposable diaper according to the present invention which is of a so-called open type design. The cover member 2 has an hourglass-shape. Tape fasteners 53 extend laterally from transversely opposite side edges of the rear waist region 7. Each of the fasteners 53 is provided at its distal end with a hook member 52 of the mechanical fastener known by the trademark of VELCRO, etc. To wear the diaper, the respective hook members 52 may be anchored on the associated loop members (not shown) of the mechanical fastener provided on the outer surface of transversely opposite side edges of the front waist region 6 so as to connect the front and rear waist regions to each other. Each of the loop members may extend to the middle of the front waist region 6 if desired so as to enlarge an area in which the hook member can be anchored.

According to the present invention, a nonwoven fabric, a plastic sheet, a rubber sheet or the like may be used as material for the cover member 2. The topsheet 22 of the liquid-absorbent member 3 may be formed from a nonwoven fabric, a porous plastic sheet or the like and the backsheet 23 may be formed from a plastic sheet, a rubber sheet or the like. The liquid-absorbent core 24 may be formed from a fluff pulp or a mixture of fluff pulp and polymer of high absorptivity. The disposable diaper according to the invention allows at least the liquid-absorbent member to be formed as compact as possible so that the cover member as well as the liquid-absorbent member closely contacts the wearer's body over an excessively large area without creating uncomfortable stuffiness. The size and shape of the cover member used to cover the liquid-absorbent member can be selected to maintain a breathable gap between the cover member and the wearer's body. In this manner, the present invention provides a comfortable disposable diaper while minimizing the possibility of the diaper becoming stuffy.

What is claimed is:

1. A disposable diaper comprising:
   a cover member having a front waist region, a rear waist region and a crotch region extending therebetween, transversely opposite side edges of said crotch region being curved inwardly so that said cover member has an hourglass-shape when said front waist region, rear waist region and crotch region are laid flat;
   a liquid-absorbent member having longitudinally opposite ends and composed of a liquid-permeable topsheet, a liquid-impermeable backsheet and a liquid-absorbent core disposed therebetween, said liquid-absorbent member extending on the inner surface of said cover member from said crotch region toward said front and rear waist regions; and belt-shaped elastically stretchable members suspending said liquid-absorbent member from said cover member, said cover member having an elastically stretchable member extending circumferentially of the waist regions and provided along a longitudinal end of at least one of said front and rear waist regions, non-elastic transversely opposite side edges of said crotch region, and transversely opposite side edges of the front and rear waist regions which are connected to each other, said belt-shaped elastically stretchable members circumferentially extending under tension across lower portions of said front and rear waist regions lying immediately above said curved crotch region and spaced longitudinally apart from and below the elastically stretchable member of the cover member, the belt-shaped elastically stretchable members being attached to the cover member only by longitudinally opposite ends of the respective elastically stretchable members which longitudinal opposite ends are bonded to said transversely opposite side edges of the respective waist regions, and the belt-shaped elastically stretchable members being attached to the liquid-absorbent member only by longitudinally middle portions of the elastically stretchable members which longitudinally middle portions are secured to an outer surface of the liquid-impermeable backsheet, said elastically stretchable members being coupled to each other so as to form a continuous loop and the longitudinally opposite ends of the cover member being freely suspended and unconnected from the longitudinal ends of the cover member, and the elastically stretchable member of the waist regions and the elastically stretchable members of the liquid-absorbent member cooperating so that when the diaper is worn, the elastically stretchable members of the liquid-absorbent member prevent the liquid-absorbent member from slipping in the event that the elastically stretchable member of the waist regions slips down on the wearer.

2. The disposable diaper according to claim 1, wherein said cover member is made of a nonwoven fabric having an elastic stretchability circumferentially of the waist regions.

3. The disposable diaper according to claim 1, wherein said cover member defines a pair of shorts in which the respective transversely opposite side edges of said front and rear waist regions are separably connected to each other.

4. The disposable diaper according to claim 1, wherein said cover member is provided at the transversely opposite side edges of said front and rear waist regions with means by which the transversely opposite side edges can be releasably fastened one to another.

5. The disposable diaper according to claim 1, wherein said cover member defines a pair of shorts in which the respective transversely opposite side edges of said front and rear waist regions are inseparably connected to each other.

6. A disposable diaper comprising:

a cover member having a front waist region, a rear waist region and a crotch region extending therebetween, transversely opposite side edges of said crotch region being curved inwardly so that said cover member has an hourglass-shape when said front waist region, rear waist region and crotch region are laid flat;

a liquid-absorbent member having longitudinal opposite ends and composed of a liquid-permeable topsheet, a liquid-impermeable backsheet and a liquid-absorbent core disposed therebetween, said liquid-absorbent member extending on the inner surface of said cover member from said crotch region toward said front and rear waist regions; and belt-shaped elastically stretchable member suspending said liquid-absorbent member from said cover member, said cover member having an elastically stretchable member extending circumferentially of the waist regions and provided along a longitudinal end of at least one of said front and rear waist regions, non-elastic transversely opposite side edges of said crotch region, and transversely opposite side edges of the front and rear waist regions which are connected to each other, said belt-shaped elastically stretchable members circumferentially extending under tension across lower portions of said front and rear waist regions lying immediately above said curved crotch region and spaced longitudinally apart from and below the elastically stretchable member of the cover member, the belt-shaped elastically stretchable members being attached to the cover member only by longitudinally opposite ends of the respective elastically stretchable members which longitudinally opposite ends are bonded to said transversely opposite side edges of the respective waist regions and the belt-shaped elastically stretchable member being attached to the liquid-absorbent member only by longitudinally middle portions of the elastically stretchable members which longitudinally middle portions are secured to an outer surface of the liquid-impermeable backsheet, and the longitudinally opposite ends of the cover member being freely suspended and unconnected from the longitudinal ends of the cover member, and the elastically stretchable member of the waist regions and the elastically stretchable members of the liquid-absorbent member cooperating so that when the diaper is worn, the elastically stretchable members of the liquid-absorbent member prevent the liquid-absorbent member from slipping in the event that the elastically stretchable member of the waist regions slips down on the wearer.

7. The disposable diaper according to claim 6, wherein said cover member is made of a nonwoven fabric having an elastic stretchability circumferentially of the waist regions.

8. The disposable diaper according to claim 6, wherein said cover member is provided at the transversely opposite side edges of the front and rear waist regions with means by which the transversely opposite side edges can be releasably connected to one another.

9. A disposable diaper comprising:

a cover member having a front waist region, a rear waist region and a crotch region extending therebetween, transversely opposite side edges of said crotch region being curved inwardly so that said cover member has an hourglass-shape when said front waist region, rear waist region and crotch region are laid flat;

a liquid-absorbent member having longitudinally opposite ends and composed of a liquid-permeable topsheet, a liquid-impermeable backsheet and a liquid-absorbent core disposed therebetween, said liquid-absorbent member extending on the inner surface of said cover member from said crotch region toward said front and rear waist regions; and belt-shaped elastically stretchable members suspending said liquid-absorbent member from the cover member, said cover member having an elastically stretchable member extending circumferentially of the waist regions and provided along a longitudinal end of at least one of said front and rear waist regions, non-elastic transversely opposite side edges of said crotch region, and transversely opposite side edges of the front and rear waist regions which are connected to each other, said belt-shaped elastically stretchable members circumferentially extending under tension across lower portions of said front and rear waist regions lying immediately above said curved crotch region and spaced longitudinally apart from and below the elastically stretchable member of the cover member, the belt-shaped elastically stretchable members being attached to the cover member only by longitudinally opposite ends of the respective elastically stretchable members which longitudinally opposite ends are bonded to said transversely opposite side edges of the respective waist regions, and the belt-shaped elastically stretchable members being attached to the liquid-absorbent member only by longitudinally middle portions of the elastically stretchable members which longitudinally middle portions are secured to an outer surface of the liquid-impermeable backsheet, said elastically stretchable members being coupled to each other so as to form a continuous loop and the longitudinally opposite ends of the cover member being freely suspended and unconnected from the longitudinal ends of the cover member, and said crotch region extending between the front and rear waist regions exclusive of portions of said front and rear waist portions where the elastic stretchable members are provided, the elastically stretchable member of the waist regions and the elastically stretchable members of the liquid-absorbent member cooperating so that when the diaper is worn, the elastically stretchable members of the liquid-absorbent member prevent the liquid-absorbent member from slipping in the event that the elastically stretchable member of the waist regions slips down on the wearer.

10. A disposable diaper comprising:

a cover member having a front waist region, a rear waist region and a crotch region extending therebetween, transversely opposite side edges of said crotch region being curved inwardly so that said cover member has an hourglass-shape when said front waist region, rear waist region and crotch region are laid flat;

a liquid-absorbent member having longitudinally opposite ends and composed of a liquid-permeable topsheet, a liquid-impermeable backsheet and a liquid-absorbent core disposed therebetween, said liquid-absorbent member extending on the inner surface of said cover member from said crotch region toward said front and rear waist regions; and belt-shaped elastically stretchable members suspending said liquid-absorbent member from the cover member, said cover member having an elastically stretchable member extending circumferentially of the waist regions and provided along a longitudinal end of at least one of said front and rear waist regions, non-elastic transversely opposite side edges of said crotch region, and transversely opposite side edges of the front and rear waist regions which are connected to each other, said belt-shaped elastically stretchable members circumferentially extending under tension across lower portions of said front and rear waist regions lying immediately above said curved crotch region and spaced longitudinally apart from and below the elastically stretchable member of the cover member, the belt-shaped elastically stretchable members being attached to the cover member only by longitudinally opposite ends of the respective elastically stretchable members which longitudinal opposite ends are bonded to said transversely opposite side edges of the respective waist regions and the belt-shaped elastically stretchable member being attached to the liquid-absorbent member only by longitudinally middle portions of the elastically stretchable members which longitudinally middle portions are secured to an outer surface of the liquid-impermeable backsheet, backsheet, and the longitudinally opposite ends of the cover member being freely suspended and unconnected from the longitudinal ends of the cover member, and said crotch region extending between the front and rear waist regions exclusive of portions of said front and rear waist portions where the elastic stretchable members are provided, the elastically stretchable member of the waist regions and the elastically stretchable members of the liquid-absorbent member cooperating so that when the diaper is worn, the elastically stretchable members of the liquid-absorbent member prevent the liquid-absorbent member from slipping in the event that the elastically stretchable member of the waist regions slips down on the wearer.

* * * * *